United States Patent [19]

Madray

[11] 4,228,935

[45] Oct. 21, 1980

[54] GLOVES AND HOLDING RACK THEREFOR

[76] Inventor: Robert M. Madray, P.O. Box 401, Blackshear, Ga. 31516

[21] Appl. No.: 868,509

[22] Filed: Jan. 11, 1978

[51] Int. Cl.$^2$ ............................................. A47J 51/06
[52] U.S. Cl. ................................... 223/111; 2/161 R
[58] Field of Search ................ 223/111; 2/168, 161 R

[56] References Cited

U.S. PATENT DOCUMENTS

| | | | |
|---|---|---|---|
| 1,996,377 | 4/1935 | Hinchen | 223/111 |
| 2,106,348 | 1/1938 | Hall et al. | 2/168 |
| 2,741,410 | 4/1956 | LaViolette | 223/111 |
| 4,069,913 | 1/1978 | Harrigan | 223/111 X |

*Primary Examiner*—Louis Rimrodt

[57] ABSTRACT

Gloves subject to contamination are handled and retained on a holding rack by first mechanically engaging and retaining the gloves in an aperture provided in the rack, restraining the wrist portion of the glove for movement in the direction of movement of a hand being inserted into the glove, and also restraining the wrist portion of the glove relative to the rack for movement in the direction of movement of a hand being withdrawn from the glove so as to permit the hand to be removed from the glove without turning the glove inside-out.

1 Claim, 2 Drawing Figures

GLOVES AND HOLDING RACK THEREFOR

BACKGROUND OF THE INVENTION

1. Field of the Invention

This invention relates generally to the handling of contaminated gloves, and the like, and particularly to specially constructed gloves in a rack for holding same, which gloves can be put on and taken off of a user's hands without necessity of touching the outer surfaces of the contaminated gloves.

2. Description of the Prior Art

When handling various contaminated and toxic materials, it is desirable that protective gloves be worn on the hands of a worker, and that these gloves be put on in an easy manner without the necessity of touching the outer surfaces of the gloves at any time. This is particularly true in industries where the gloves are used repeatedly between cleanings.

U.S. Pat. No. 2,741,410, issued Apr. 10, 1956, to F. G. LaViolette, discloses apparatus for handling contaminated gloves wherein a collar at the wrist of the gloves embraces the surfaces surrounding an aperture provided in a shelf and the hand is pulled downwardly through the aperture in order to strip the hand of the glove while turning the glove inside-out. The glove is subsequently turned right-side out by use of a suction created within a rectification and inflation compartment of a vacuum machine. In order words, the method as set for in U.S. Pat. No. 2,741,410 for handling contaminated gloves involves a two-step operation and the use of expensive machinery in order to strip the glove from one's hand and subsequently have the glove arranged for reinsertion of a hand.

U.S. Pat. Nos. 1,938,685, issued Dec. 12, 1933, to H. E. Breuls, et al., and 3,695,493, issued Oct. 3, 1972, to R. J. Karr, disclose further examples of vacuum devices employed for removing surgical gloves, while U.S. Pat. No. 3,237,821, issued Mar. 1, 1966, to R. E. Hayne, et al., discloses a glove changing arrangement based on the glove port of a glove box employed for disposing of gloves contaminated by radioactive and similar hazardous materials.

U.S. Pat. No. 3,555,564, issued Jan. 19, 1971, to E. Miskell, et al., discloses a rubber surgical glove provided with a thickened cuff portion which, when pulled over the end of a loose, bulky sleeve, forms a ring of bunched-up sleeve material between two spaced thickened bands formed on the cuff portion of the glove. This ring of bunched-up sleeve material prevents the cuff portion from slipping and working down off the sleeve of the workman toward the hand of same.

SUMMARY OF THE INVENTION

It is an object of the present invention to provide gloves and holding rack therefor which permits the gloves to be put on and removed without the gloves being turned inside-out, and without necessity of touching the outside surfaces of the gloves.

It is another object of the present invention to provide gloves and holding rack therefor which is especially suited for use with gloves contaminated by materials of a nature which does not require disposal of the gloves after each use.

It is still another object of the present invention to provide gloves and a holding rack therefor which permit the gloves to be put on and taken off in such a simple and efficient manner as to encourage workmen to use gloves when handling toxic materials, and the like.

These and other objects are achieved according to the present invention by providing a glove and a holding rack therefor wherein the rack has a support provided with a front edge from which extends an aperture shaped for receiving the wrist or cuff portion of a glove, with the glove including a wrist or cuff portion receivable in the aperture and provided with retaining elements for restraining the glove against movement relative to the support.

The support of the rack is advantageously a planar shelf in which a pair of apertures are provided for receiving the gloves of a single workman. The support also preferably includes a pair of substantially parallel, spaced side walls extending perpendicularly and codirectionally from the shelf, and jointed to a back wall extending perpendicularly from the shelf and codirectionally with and extending between the side walls. The back wall can be used to mount the rack on a supporting wall, and the like, while when the rack is to be disposed out of doors, a top is advantageously removably mounted on the back and/or side walls for forming a protective enclosure for the gloves when same as disposed on the rack.

The retaining elements of the gloves preferably are a pair of spaced, substantially parallel collars provided on the wrist portion of an associated glove, with one of the collars arrangeable above the shelf of the rack for restraining the glove against movement relative to the rack when a hand is being put into the glove, and the other of the collars being arrangeable beneath the support for restraining the associated glove against movement relative to the support, or shelf, when a workman's hand is being removed from the glove.

Each of the apertures provided in the support of the rack preferably include a slot extending from the front edge of the support, or shelf, and communicating with an enlarged portion disposed in the interior of the support. By this arrangement, the wrist of a workman can be passed along the slot so as to place the pair of collars in proper position bracketing the shelf, while the enlarged portion permits the hand of the workman to be placed into or removed from the glove thus held on the rack.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
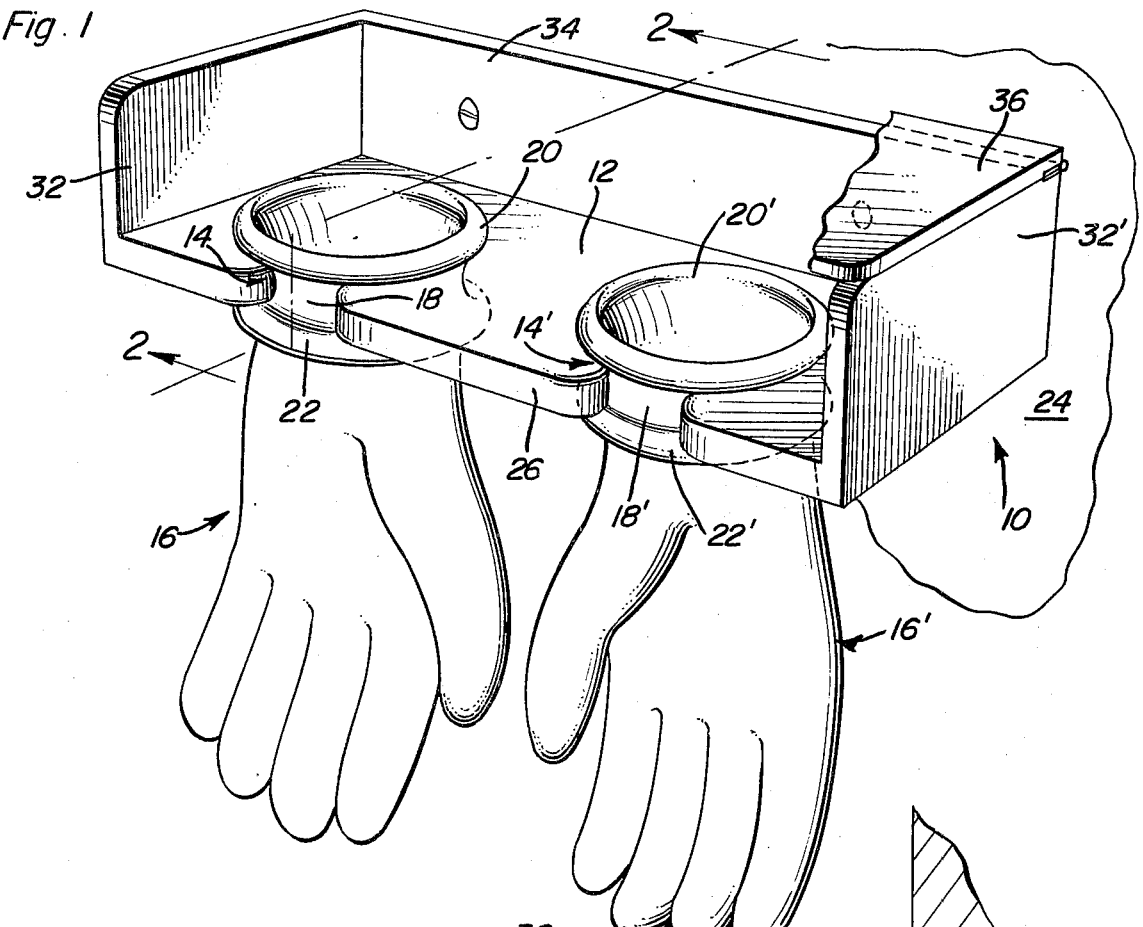
FIG. 1 is a fragmentary, perspective view showing gloves and holding rack therefor according to the present invention.

Referring now more particularly to the figures of the drawing, a holding rack 10 according to the present invention comprises a support 12 in which are provided a pair of spaced apertures 14 and 14' each shaped for receiving the wrist, or cuff, portion of gloves 16 and 16'. Each of these gloves 16, 16' includes a wrist portion 18, 18' receivable in an associated aperture 14, 14' and provided with retaining elements arranged for restraining the gloves 16, 16' against movement relative to support 12. The latter is advantageously a planar bottom wall of rack 10, the general construction of which rack 10 will be described in greater detail below.

The retaining elements of gloves 16 and 16' include a pair of spaced, substantially parallel collars 20, 22 and 20' and 22', respectively, with the collars 20, 20' arrangeable above support 12 for restraining glove 16, or more specifically wrist portion 18, against movement relative to support 12 when a hand, such as that associated with arm A is being put into the associated glove 16, 16', and the collars 22', 22' being arrangeable beneath support 12 for restraining the associated glove 16, 16' against movement relative to support 12 when the hand is being removed from the glove 16, 16'. By this arrangement, it will be appreciated that removal of a hand from an associated glove 16, 16' will not result in the glove being turned inside-out and, accordingly, the glove will remain in proper position for insertion of a hand into the glove when use of the glove is next desired. In the meantime, the glove will be stored on the rack 10.

Figure 2:
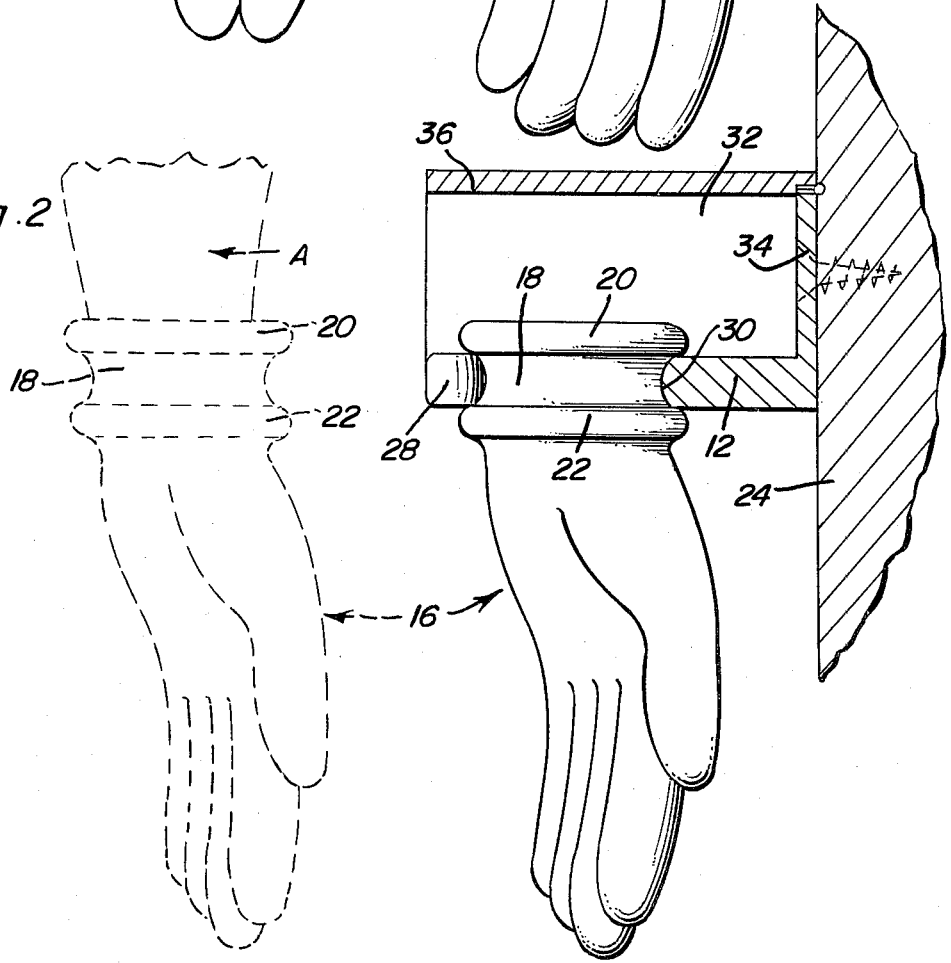
FIG. 2 is an enlarged, fragmentary, sectional view taken generally along the line 2—2 of FIG. 1.

Support 12, which advantageously extends cantilever-fashion from a conventional wall 24, such as an interior or exterior wall of a building, and terminates at the free end thereof in a longitudinally extending edge 24 in which apertures 14 and 14' are formed. More specifically, each of the apertures 14, 14' includes a slot 28 which extends perpendicularly from the extent of edge 26, and merges into an enlarged portion 30 formed in the interior of support 12. By proper design, this slot 28 permits the wrist of an arm A to pass into and out of the enlarged portion 30 in such a manner that collar 20, 20' is disposed above, or adjacent the upper surface of, support 12, and collar 22, 22' is disposed beneath, or adjacent the lower surface of, support 12. The broken line showing of glove 16 and an associated arm A in FIG. 2 shows the general orientation of a person's hand prior to inserting the glove into the associated aperture 14, or the similar position of one's arms and hands immediately after sliding a glove out of the associated aperture after insertion of a hand thereinto.

As can be appreciated from the drawings, the collars 20, 22 and 20', 22' are preferably in the form of solid toroids. Rack 10 also includes, in addition to the bottom wall or support 12, a pair of substantially parallel, spaced side walls 32 and 32' arranged extending perpendicularly and codirectionally from support 12, and a back wall extending perpendicularly from the plane of support 12 and codirectional with and extending between the side walls 32, 32'. The back wall can be employed, as illustrated, for mounting the rack 10 on a supporting wall 24, with the side walls 32, 32' giving the structure stability. Further, when the rack 10 is to be disposed out-of-doors, it is desirable, in order to protect the gloves 16, 16', when same are stored on rack 10, to provide a top 36 which can be hinged as illustrated or merely disposed sitting on the side walls 32 and 32' and back wall 34, in order to protect the gloves from rain and other environmental conditions.

As can be understood from the above description and from the drawings, a gloves and holding rack arrangement according to the present invention will provide for the puting on and taking off of contaminated gloves in a simple and efficient manner, thus encouraging workmen to use gloves when appropriate, and without the necessity of touching the outer surface of the gloves and without turning the gloves inside-out, while the rack itself can serve as a protective enclosure for the gloves when same are not being used.

The foregoing is considered as illustrative only of the principles of the invention. Further, since numerous modifications and changes will readily occur to those skilled in the art, it is not desired to limit the invention to the exact construction and operation shown and described and accordingly all suitable modifications and equivalents may be resorted to, falling within the scope of the invention.

What is claimed as new is as follows:

1. A glove and holding rack comprising in combination;
   (a) A support provided with a planar bottom wall having a free edge;
   (b) said free edge having at least one aperture shaped for receiving the wrist portion of a glove;
   (c) a pair of substantially paralled, spaced side walls extending perpendicularly and codirectionally from the bottom wall;
   (d) a back wall extending perpendicularly from the bottom wall and co-directionally with and extending between the side walls; and
   (e) a top removable mounted on the side walls and the back wall, whereby a glove having a pair of spaced, substantially parallel retaining collars, each in the form of a solid toroid, may be receivable in the aperture provided in the support, with one of the collars being arrangeable above the support for restraining the glove against movement relative to the support when a hand in being put into the glove, and the other of the collars being arrangeable beneath the support for restraining the glove against movement relative to the support when a hand is being removed from the glove.

* * * * *